United States Patent [19]

Bodmer et al.

[11] Patent Number: 5,677,425

[45] Date of Patent: Oct. 14, 1997

[54] RECOMBINANT ANTIBODY

[75] Inventors: Mark William Bodmer, Oxfordshire; John Robert Adair, High Wycombe; Nigel Richard Whittle, Surrey, all of England

[73] Assignee: Celltech Therapeutics Limited, Berkshire, United Kingdom

[21] Appl. No.: 292,356

[22] Filed: Aug. 18, 1994

Related U.S. Application Data

[63] Continuation of Ser. No. 7,022, Jan. 21, 1993, abandoned, which is a continuation of Ser. No. 810,349, Dec. 18, 1991, abandoned, which is a continuation of Ser. No. 602,380, Oct. 24, 1990, abandoned, which is a continuation of Ser. No. 353,629, filed as PCT/GB88/00730 Sep. 5, 1988, published as WO89/01974 Mar. 9, 1989, abandoned.

[30] Foreign Application Priority Data

Sep. 4, 1987 [GB] United Kingdom ................... 8720833

[51] Int. Cl.$^6$ ............................. C12N 15/00; C07K 14/00; C07K 16/00; C12P 21/08
[52] U.S. Cl. ................... 530/387.1; 530/350; 530/387.3; 530/391.1; 530/391.3; 530/866; 530/867; 435/172.3
[58] Field of Search ............................. 530/387.3, 391.3; 435/172.3

[56] References Cited

U.S. PATENT DOCUMENTS

| | | |
|---|---|---|
| 4,751,077 | 6/1988 | Bell ........................................... 424/85 |
| 4,816,567 | 3/1989 | Cabilly et al. ........................... 530/387 |

FOREIGN PATENT DOCUMENTS

| | | |
|---|---|---|
| 0 146 413 | 6/1985 | European Pat. Off. . |
| 0146413 | 6/1985 | European Pat. Off. . |
| WO A 86/01533 | 3/1986 | WIPO . |

OTHER PUBLICATIONS

Oi et al Nature 307: 136,1984.
Morrison, Science 229: 1202,1985.
Oi et al., "Correlation Between Segmental Flexibility and Effector Function of Antibodies" Nature 307: 136–140 (1984).
Morrison, "Transfectomas Provide Novel Chimeric Antibodies" Science 229: 1202–1207 (1985).
Krawinkel and Rabbitts, "Comparison of the Hinge–Coding Segments in Human Immunoglobulin Gamma Heavy Chain Genes and the Linkage of the Gamma 2 and Gamma 4 Subclass Genes", Embo Journal 1: 403–407 (1982).
Krawenhel et al EMBO J 1:403,1982.
Stites in Basic & Clinical Immunology, 1984, pp. 30–42.
WO, A, 86/01533 (Celltech) 13 Mar. 1986 )cited in the application).

*Primary Examiner*—Suzanne E. Ziska
*Attorney, Agent, or Firm*—Woodcock Washburn Kurtz Mackiewicz & Norris

[57] ABSTRACT

The present invention provides an altered antibody molecule (AAM) having a hinge region which has a different number of cysteine residues from that found in the hinge region normally associated with the CH1 domain of the antibody molecule and a process for producing the same using recombinant DNA technology.

13 Claims, 1 Drawing Sheet

HINGE AMINO ACID SEQUENCES.

| | | | |
|---|---|---|---|
| IgG1 | EAPKSCDKTH | TCPPCP | 2 cysteine hinge |
| IgG2 | ERKCCVECPP* | CP | 4 cysteine hinge |
| IgG3 | ELKTPLGDTT | HTCPRCPERK | 11 cysteine hinge |
| | CPEPKSCDTP | PPCPRCPEPK | |
| | | SCDTPPPCPR | |
| IgG4 | ESKYGPPCPS | CP | 2 cysteine hinge |

\* This cysteine is bridged to the light chain.

RECOMBINANT ANTIBODY

This is a continuation, of application Ser. No. 08/007, 022, filed Jan. 21, 1993 now abandoned, which is a continuation of application Ser. No. 07/810,349 filed Dec. 18, 1991, now abandoned, which is a continuation of application Ser. No. 07/602,380, filed Oct. 24, 1990, now abandoned, which is a continuation of application Ser. No. 07/353,629, filed Jun. 30, 1989, now abandoned, of PCT/GB88/00730, filed Sep. 5, 1988, originally filed as United Kingdom Ser. No. 87 20833 on Sep. 4, 1987 published as WO89/01974 Mar. 9, 1989.

The present invention relates to an altered antibody molecule (AAM) having an altered number of cysteine residues in its hinge region and to a process for its production using recombinant DNA technology.

In the present application:

the term "MAb" is used to denote a monoclonal antibody;

the term "recombinant antibody molecule" (RAM) is used to describe an antibody produced by any process involving the use of recombinant DNA technology, including any analogues of natural immunoglobulins or their fragments; and the term "humanised antibody molecule" (HAM) is used to describe a molecule having an antigen binding site derived from an immunoglobulin from a non-human species, the remaining immunoglobulin-derived parts of the molecule being derived from a human immunoglobulin. The antigen binding site may comprise either complete variable domains fused onto constant domains or only the complementarity determining regions (CDRs) grafted onto appropriate framework regions in the variable domains.

In the description, reference is made to a number of publications by number. The publications are listed in numerical order at the end of the description.

Natural immunoglobulins have been known for many years, as have the various fragments thereof, such as the Fab, (Fab')$_2$ and Fc fragments, which can be derived by enzymatic cleavage. Natural immunoglobulins comprise a generally Y-shaped molecule having an antigen-binding site at the end of each arm. The remainder of the structure, and particularly the stem of the Y, mediates the effector functions associated with immunoglobulins.

At the junction of the arms of the Y-shaped molecule, there is an area known as the hinge region. In this region there are, depending on the class of the antibody, between 2 and 11 inter-heavy chain disulphide bonds. These disulphide bonds are responsible for holding together the two parts of the complete antibody molecule. In a Fab fragment, the hinge region has been enzymatically separated from the antigen banding region. Thus, the Fab fragment comprises a light chain/truncated heavy chain dimer. However, in the (Fab')$_2$ fragment, the Fc portion is cleaved off the antigen binding regions on the C-terminal side of the hinge region. Thus, the (Fab')$_2$ fragment comprises two light chain/truncated heavy chain dimers held together in a tetrameric structure by the hinge region.

The hinge region allows the arms of the Y-shaped antibody molecule to move relative to one another. It is conjectured that the degree of movement is determined to a large extent by the number of disulphide bonds in the hinge region. It is also believed that the hinge region plays a key role in the transmission of conformational changes from the antigen binding regions to the Fc portion of the molecule. Such conformational changes may be necessary in order to activate the effector functions of the immunoglobulin molecule.

In natural antibodies, in particular the IgGs, the hinge represents a distinct region of the antibody, at both the protein and gene level. High resolution date on the in vivo conformation of the hinge region are not available from the structural studies performed to date. However, model building suggests that the hinge regions may form a relatively simple extended or helix-like structure linked by disulphide bridges.

Natural immunoglobulins and their fragments have been used in diagnosis and, to a more limited extent, in therapy. However, such uses, especially in therapy, have been hindered by the polyclonal nature of natural immunoglobulins. A significant step towards the realisation of the potential of immunoglobulins as therapeutic agents was the discovery of monoclonal antibodies (1) of defined antigen specificity. Most MAbs are produced by fusions of rodent spleen cells with rodent myeloma cells. They are therefore essentially rodent MAbs. There are very few reports of the production of human MAbs.

There have been made proposals for "humanizing" rodent MAbs. These techniques generally involve the use of recombinant DNA technology to manipulate DNA sequences encoding the polypeptide chains of the antibody molecule. Some early methods for carrying out such a procedure are described in EP-A-0 171 496 (Res. Dev. Corp. Japan), EP-A-0 173 494 (Stanford University), EP-A-0 194 276 (Celltech Limited) and WO-A-8 702 671 (Int. Gen. Eng. Inc.).

In an alternative approach, described in EP-A-87302620.7 (Winter), the complementarity determining regions (CDRs) of a mouse MAb have been grafted onto the framework regions of the variable domains of a human immunoglobulin by site directed mutagenesis using long oligonucleotides.

It has been widely suggested that immunoglobulins, and in particular MAbs, could potentially be very useful in the diagnosis and treatment of cancer (2,3). There has therefore been much activity in trying to produce immunoglobulins or MAbs directed against tumour-specific antigens. So far, over one hundred MAbs directed against a variety of human carcinomas have been used in various aspects of rumour diagnosis or treatment (4).

In our copending, concurrently filed U.S. application Ser. No 353,632 there is described a humanised antibody molecule (HAM) having an antigen binding site wherein at least the complementarity determining regions (CDRs) of the variable domain are derived from the mouse monoclonal antibody B72.3 (B72.3 MAb) and the remaining immunoglobulin-derived parts of the HAM are derived from a human immunoglobulin, and a process for its production.

The B72.3 MAb is a mouse MAb of the type IgG1-Kappa raised against a membrane-enriched extract of a human liver metastatis of a breast carcinoma (5). The B72.3 MAb has been extensively studied in a number of laboratories. It has been shown to recognise a tumour-associated glycoprotein TAG-72, a mucin-like molecule with a molecular weight of approximately $10^6$ (6). Immunohistochemical studies have demonstrated that the B72.3 MAb recognises approximately 90% of colorectal carcinomas, 85% of breast carcinomas and 95% of ovarian carcinomas. However, it shows no significant cross-reactivity with a wide spectrum of normal human tissues (7 to 10).

It has been suggested, for instance in EP-A-0 194 276, that effector or reporter molecules may be attached to an antibody or a fragment thereof in order to increase its effectiveness as a therapeutic or diagnostic agent. The attachment may be by means of a covalent bridging structure. Alternatively, where the effector or reporter molecule is a protein, it may be coexpressed as the C-terminal part of a fusion protein, the N-terminal part of which comprises at least the variable domain of one of the chains of the antibody molecule or fragment.

In all the work carried out so far, the hinge region, if present, in the antibody molecule or fragment has been that normally associated with the CH1 domain of the antibody molecule. There has been no suggestion that the hinge region should in any way be altered except in so far as it may be necessary to alter its C- or N-terminal sequence to facilitate manipulations by recombinant DNA technology.

According to a first aspect of the present invention, there is provided an altered antibody molecule (AAM) having a hinge region which has a different number of cysteine residues from that found in the hinge region normally associated with the CH1 domain of the antibody molecule.

The AAM of the present invention may comprise: a complete antibody molecule, having full length heavy and light chains; an (Fab')$_2$ fragment; or any other fragment including a hinge region. The antigen binding portions of the AAM may, if desired, have different specificities, the antibody in this case being bispecific.

The AAM of the present invention may have attached to it an effector or reporter molecule. For instance, the AAM may have a macrocycle, for chelating a heavy metal atom or a toxin, such as ricin, attached to it by a covalent bridging structure. Alternatively, the procedures of recombinant DNA technology may be used to produce a AAM in which the Fc fragment or CH$_3$ domain of a complete antibody molecule has been replaced by an enzyme or toxin molecule.

Preferably, the AAM of the present invention is also a HAM, for instance of the type described in the above-referenced copending application. The variable domains of the HAM may comprise either the entire variable domains of a rodent MAb or may comprise the framework regions of a human variable domain having grafted thereon the CDRs of the rodent MAb. The remainder of the HAM may be derived from any suitable human immunoglobulin. However, it need not comprise only protein sequences from the human immunoglobulin. For instance, a gene may be constructed in which a DNA sequence encoding part of a human immunoglobulin chain is fused to a DNA sequence encoding the amino acid sequence of a polypeptide effector or reporter molecule.

The altered hinge region of the AAM of the present invention may comprise a complete hinge region derived from an antibody of different class or subclass from that of the CH1 domain. Thus, for instance, a CH1 domain of class γ 1 may be attached to a hinge region of class γ 4. Alternatively, the new hinge region may comprise part of a natural hinge or a repeating unit in which each unit in the repeat is derived from a natural hinge region. In a further alternative, the natural hinge region may be altered by converting one or more cysteine residues into neutral residues, such as alanine, or by converting suitably placed residues into cysteine residues. It can thus be seen that the number of cysteine residues in the hinge region may be increased or decreased.

In one preferred aspect of the invention, the number of cysteine residues in the hinge region is reduced to one. This will have the advantage that it will facilitate assembly of the antibody molecules, particularly bispecific antibody molecules and antibody molecules wherein the Fc portion has been replaced by an effector or reporter molecule, since it will only be necessary to form a single disulphide bond. This will provide a specific target for attaching the hinge region either to another hinge region or to an effector or reporter molecule, either directly or indirectly, by chemical means.

In alternative preferred aspect, the number of cysteine residues in the hinge is increased. The advantage of this is that it will faciliate the use of the cysteine thiol groups for attaching effector or reporter molecules to the AAM. For instance, 99m technecium, a radiolabel, may be attached to hinge cysteines either directly or by use of a macrocycle ligand as described in our copending British application Nos. 8800843 and 8812257. Increasing the number of cysteines can also be used to stabilize the interactions between adjacent hinges.

It will be appreciated by the skilled person that the present invention enables him to make an informed trade-off between improved specificity of attachment and assembly on the one hand and improved stability and decreased specificity on the other hand.

Preferably, the AAM of the present invention is produced by recombinant DNA technology. Therefore, according to a second aspect of the present invention, there is provided a process for producing an AAM according to the first aspect of the invention, which process comprises:

(a) producing in an expression vector an operon which includes a DNA sequence encoding an antibody heavy chain having a hinge region which has a different number of cysteine residues from that found in the hinge region normally associated with the CH1 domain of the antibody molecule.

The operon may be produced by splicing a DNA sequence encoding the CH1 region from an antibody of one class to a DNA sequence encoding the hinge region from an antibody of a different class.

Alternatively, the operon may be produced by cloning the CH1 domain and hinge region from an antibody of one class and altering the number of cysteine residue encoding DNA triplets by site directed mutagenesis. Preferably, where the number of cysteine residues is to be decreased, the cysteine-encoding sequence are mutated to alanine-encoding sequences. Where the number of cysteine-encoding sequences is to be increased, any suitable positioned non-cysteine residue may be altered.

Preferably, the process of the second aspect of the invention includes the steps of:

(b) transfecting a cell line with the vector; and (c) culturing the transfected cell line to produce the AAM.

In the process of the second aspect of the present invention, as the vector encodes only the heavy chain antibody polypeptide it will be necessary to arrange for the cell line to produce a complementary light chain. In order to achieve this, one of three alternative strategies may be employed.

In the first alternative, the cell line may be transfected with a second vector, the second vector encoding a complementary light chain-derived polypeptide. Preferably, the vectors are identical except in so far as the coding sequences and selectable markers are concerned so as to ensure as far as possible that each polypeptide chain is equally expressed.

In the second alternative, the vector may include sequence coding for both light chain-and heavy chain-derived polypeptides.

In the third alternative, it is possible to produce the AAM by using a host cell which naturally secretes a complementary light chain.

The present invention also includes cloning and expression vectors and transfected cell lines used in the process of the invention, therapeutic and diagnostic compositions containing the AAM of the invention and used of such compositions in therapy and diagnosis.

The general methods by which the vectors may be constructed, transfection methods and culture methods are well known pre se and form no part of the invention. Such methods are shown, for instance, in reference 11 and 12.

The present invention is now described, by way of example only, with reference to the accompanying drawing which shows the natural amino acid sequences of the four human IgG hinge regions.

In our above referenced copending, concurrently filed U.S. application Ser. No 353,632 we describe in detail the production of humanized antibody molecules based on the B72.3 MAb and in particular, the construction of whole antibody molecules and F (ab') fragments is shown. The application describes the construction of various expression vectors and their use in producing humanised B72.3 antibodies (B72.3 HAMs). This work forms the basis for the work now described.

Figure 1:
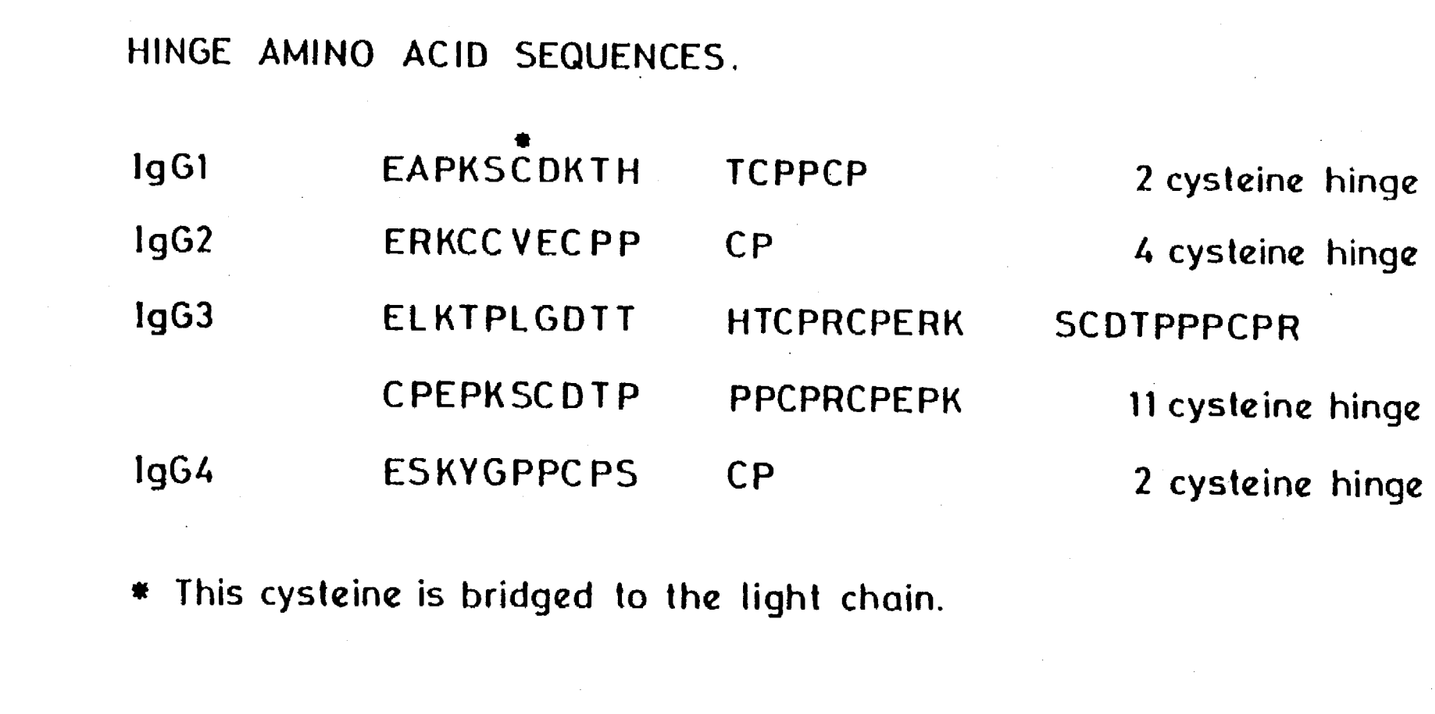

Natural human IgGs can have one of four possible hinge regions. The amino acid sequences of these hinge regions are shown in the accompanying drawing. From the known amino acid sequence it will readily be possible for the skilled person to design or mutate oligonucleotides to encode these sequences, or variants thereof with cysteine additions or deletions.

EXAMPLE 1

In Example 3 of U.S. Ser. No 353,632, there is described an (Fab')$_2$ molecule having the B72.3 variable domains and a human IgG4 CH1 domain and hinge region. In order to encourage selective reduction at the hinge of this B72.3 HAM and to reduce the complexity of subsequent chemical additions at the hinge, the number of cysteines in the B72.3 HAM hinge region (which is normally two) was reduced to one by replacing the second hinge cysteine residue with an alanine residue.

A part of the amino acid sequence of the hinge region and its corresponding DNA encoding sequence is shown below.

| CCC | CCA | TGC | CCA | TCA | TGC | CCA |
|-----|-----|-----|-----|-----|-----|-----|
| Pro | Pro | Cys | Pro | Ser | Cys | Pro |

Molecular Cloning and sequencing of the B72.3 heavy and light chain cDNAs.

Polyadenylated DNA was isolated from the B72.3 hybridoma cell line using the guanidium isothiocyanate/caesium chloride method (Maniatis et al, Molecular Cloning, Cold Spring Harbour, N.Y., 1982). Double stranded cDNA was synthesised (Gubler and Hoffman, Gene 25, 263–269, 1984) and a cDNA library was constructed in bacteriophage λ gt 10 vector using EcoRI linkers (Huynh et al, Practical Approaches in Biochemistry, IRL Oxford (Ed. Glover, M. M.) 1984). Two screening probes were synthesised, complementary to mouse immunoglobulin heavy and light chain constant regions. The heavy chain probe was a 19 mer complementary to residues 115–133 in the CH1 domain of the mouse 1 sequence (Honjo et al, Cell 18, 559–568, 1979). The light chain probe was on 20-mer complementary to residues 4658–4677 of the genomic mouse CK sequence (Max et al, J. Biol. Chem. 256, 5116–5120, 1981). The probes were radio-labelled at the 5' terminus with [γ $^{32}$P] ATP using T4 polynucleotide kinase (Amersham International) and used to screen the cDNA library.

Clones which contained the complete leader, variable and constant regions of both the heavy and light chains were isolated. The EcoRI cDNA inserts were subcloned into M13mp8 vectors for sequencing (Messing and Vieira, Gene 19, 269–276, 1982), generating a heavy chain clone, designated pBH41, and a light chain clone, designated pBL52. Nucleotide sequence analysis was carried out according to the chain termination procedure (Sanger et al, PNAS 74, 5463–5467, 1977).

The 980 base pair EcoRI insert in pBL52 was fully sequenced (Sanger et al, PNAS 74, 5463–5467, 1977). The EcoRI insert in pBH41 was shown to comprise approximately 1700 base pairs by agarose gel electrophoresis. The variable domain and the 5' region of the CH1 domain were sequenced, as was the 3' end of the clone to confirm the presence of the correct mouse γ 1 termination sequences. The DNA and predicted amino acid sequences for the unprocessed variable regions of pBH41 and pBL52 are shown in FIG. 1. Examination of the derived amino acid sequence revealed considerable homology with other characterized immunoglobulin genes, and enabled the extent of the leader, variable and constant domains to be accurately determined. In addition, Mab B72.3 was confirmed to be an IgG1 K antibody, as previously reported (Colcher et al, PNAS 78, 3199–3203, 1981).

Construction of the Chimeric Mouse-Human Heavy Chain Clone

A genomic clone containing sequences coding for the human C γ 4 region was isolated as a HindIII fragment from the cosmid COS Ig8 (Krawinkel and Rabbits, EMBO J. 1, 403–407, 1982) and then cloned via pAT153 into M13tg130 as an EcoRI-BamHI fragment to form pJA78. Following DNA sequence analysis, an 18 mer oligonucleotide was synthesised and site specific mutagenesis was performed to convert a C residue to an A residue, thereby generating a novel HindIII site at the start of the CH1 exon, to yield pJA91.

Site directed mutagenesis was performed (Kramer et al, Nucl. Acids Res. 12, 9441–9446, 1984) using EcoRI- and BglI-cut M13mp18 to generate a gapped duplex with the relevant phage template. DNA was transformed into E. coli HB2154 and resultant transformants were propagated on E. coli HB2151 (Anglian Biotechnology Ltd) as described in the protocols provided. All mutations were sequenced using the chain termination procedure (Sanger et al, PNAS 74, 5463–5467, 1977). All sequenced fragments were subsequently recloned into other vectors in order to exclude the possibility of secondary mutations which may have occurred during the mutagenesis procedure.

The VH domain from the B72.3 heavy chain cDNA, cloned in M13mp9 as pBH41, was isolated as an EcoRI-BglII fragment and introduced into the EcoRI-HindIII sites of pJA91 in conjunction with a 32 base pair Bg-II-HindIII adaptor to yield pJA93. The product was therefore a chimeric immunoglobulin heavy gene containing a variable region derived from a mouse cDNA clone fused to a sequence, comprising the CH1 , H, CH2 and CH3 domains separated by introns, derived from a human genomic clone. The accuracy of the variable/constant region junction was confirmed by nucleotide sequence analysis. The γ 4 constant region was selected as it possesses a limited number of effector functions, but does bind to Staphylococcal Protein A, a potentially useful reagent for purification.

Construction of the Chimeric Mouse-Human Light Chain Gene

The mouse light chain cDNA clone, pBL5, contains a cutting site for MboII 18 base pairs downstream from the junction of the variable and constant domains. Due to sequence homology between the mouse and human CK genes, an identical cutting site exists in the latter gene (Hieter, et al, Cell 22, 197-207, 1980) and use of this site provides a method of fusing the mouse variable and human constant domains. Partial digestion of the EcoRI fragment containing the mouse cDNA clone with MboII generated a 416 base pair EcoRI-MboII fragment with a single residue overhang. A genomic clone, comprising an M13-derived vector containing the human C-kappa gene on a PstI-HindIII fragment was digested with FokI. A 395 base pair fragment containing the majority of C-kappa was cloned into pAT153 using EcoRI linkers to form pNW200. Digestion of a 945 base pair ScaI-HindIII fragment from pNW200 with MboII generated a 374 base pair MboII-HindIII fragment, which could anneal with and be ligated to the 416 base pair EcoRI-MboII fragment described above. The two fragments were ligated into a pSP64 vector linearised with EcoRI and HindIII, and used to transform competent E. coli HB101. The variable/constant region junction was sequenced in order to confirm the correct fusion.

Construction of Expression Vectors for Transient Expression in COS Cells

The heavy and light chain chimeric genes, as well as the mouse heavy and light chain cDNA clones, were inserted separately into the unique EcoRI site of plasmid pEE6 (Whittle et al, Prot. Eng. 1, 6, 499-505, 1987). The light chain encoding plasmid was designated EE6.cL.neo. For the chimeric heavy chain, this was accomplished by using an oligonucleotide adapter to change the 3' BamHI site to an EcoRI site to give an EcoRI fragment for cloning. The heavy chain encoding plasmid was designated EE6.cH.gpt. (also designated as JA96). This plasmid contains the strong promoter/enhancer and transcriptional control element from the human cytomegalovirus (hCMV) inserted into a unique HindIII site upstream of the EcoRI site. In addition, an SV40 origin of replication site is provided by the SV40 early promoter which derives a selectable marker gene, either a neomycin-resistance gene (neo) for light chain gene or a guanine phosphoribosyl transferase gene (gpt) for heavy chain genes, inserted into a unique BamHI site. The plasmid also contains an ampicillin-resistance gene allowing selection and propagation in bacterial hosts.

Chimeric B72.3 IgG4 F(ab')$_2$
Construction of F(ab') Heavy Chain Gene
Assembly of F(ab') Gene pJA79 is an M13tg130 vector which contains the human IgG4 heavy chain gene modified so that the sequence from the first nucleotide after the last codon of the hinge exon to the last nucleotide of the CH3 domain inclusive has been removed by oligonucleotide directed site specific deletion. The hinge and 3' untranslated region and part of the M13 sequence can be isolated as a 1.1 kbp Bg-III fragment. This fragment can be used to replace the analogous fragment in the full length B72.3/IgG4chimeric heavy chain gene clone pJA93to give plasmid JA94 which therefore contains a chimeric gene potentially capable of being expressed to produce a B72.3 IgG4 chimeric F(ab') heavy chain protein.

Reconstruction of IgG4 F(ab') Heavy Chain Gene
Assembly of F(ab') Gene pJA94 described above was derived from pJA93which in turn was derived from pJA91. This clone was initially an M13 tg130 based vector, i.e. an amber phage capable of being used in the efficient gap-heteroduplex mutagenesis procedure described earlier. In order to repeat the mutagenesis procedure at high yield, the chimeric F(ab') heavy chain gene was isolated as an ECOR1 fragment and recloned into M13 tg130 to give pJA100. By oligonucleotide directed site specific mutagenesis, a SalI site was introduced towards the 3' end of the CH1 exon to give pJA108. The introduced SalI site in the CH1 domain codes for the fifth and fourth from last amino acids of the CH1 domain.

Modified B72.3 Chimeric IaG4(Fab')$_2$
Single Cysteine IgG4 Hinge
Construction and Assembly of Modified F(ab') Gene To construct a modified hinge onto the end of the CH1 domain in pJA108, four oligonucleotides were made which together are able to code for the last five amino acids of the CH1 domain, the hinge sequence, two inframe stop codons and an EcoRI site.

The oligonucleotides required to form the new Cys-Ala modified hinge sequence have the following sequences:

---

1
5' TCGACAAGAGACTTGAGTCCAAATATGGG
3' GTTCTCTCAACTCAGGTTTATACCCGGGGG
2
3
5' CCCCCGTGCCCATCAGCCCCATGATG
3' CACGGGTAGTCGGGGTACTACTTAA
4

---

Oligonucleotides 1 and 3 were used to form the sense strand and oligonucleotides 2 and 4 were used to form the antisense strand.

The modified CH1/hinge region junction encoded by the modified gene has the amino acid sequence:

---

Lys Val Asp Lys Arg Val Glu Ser Lys Tyr Gly Pro Pro
Cys Pro Ser Ala Pro Stop Stop

---

The CH1/hinge region junction is between the Val and Glu residues.

The oligonucleotides were assembled and cloned into M13 mp11 between the SalI and EcoRI sites in the polylinker, sequenced, reisolated and ligated to the gene containing the EcoRI - SalI 700bp fragment from pJA108 to construct the modified (hinge cys to ala) chimaeric B72.3 F(ab') heavy chain gene.

Assembly of Gene in Expression Vector

The modified chimaeric B72.3 F(ab') heavy chain gene fragment, assembled as described above, was subsequently cloned into the EcoRI vector fragment of pJA96 to give pgA115.

Test of Genes in COS Cells

The genes were tested in COS cells as described in the PA149 application. On non-reducing SDS-PAGE the material appeared to be produced as F(ab') material only. Reducing SDS-PAGE the material appeared to be produced as F(ab') material only. Reducing SDS-PAGE showed the presence of light chain and truncated heavy chain equivalent to that expected from the modified F(ab') gene.

Development of Stable Cell Lines in CHO Cells

The expression plasmid pJA115, comprising the hinge modified B72.3 chimaeric F(ab') heavy chain gene fragment expressed from the HCMV promoter, was introduced by electroporation into the CHO cell line cL18 described in the PA149 application. The procedure was similar to that described for introduction of the full length chimaeric heavy chain except that the SalI digestion was omitted and the DNA was introduced as closed circular DNA. Cell lines resistant to mycophenolic acid and expressing functional modified F(ab') antibody was identified by screening culture supernatants in an antigen binding ELISA format assay as described earlier. Cell lines expressing between 0.1–10 µg/ml modified F(ab') were isolated. One cell line, 18ΔF9, was used for further studies.

CHO cell lines expressing the modified F(ab') were also isolated using gene amplification. A plasmid vector comprising the chimaeric light chain and modified F(ab') heavy chain gene fragment, each expressed separately from the HCMV promoter, and the glutamine synthetase (GS) minigene described in our International patent application No. PCT/GB88/00602, namely pEE6.cH.cL.GS, was introduced into CHO-K1 cells by the calcium phosphate precipitation procedure.

Transfectants were selected in GMEM medium as described in our International patent application No. PCT/GB88/00602 comprising 20 µM methionine sulphoximine (MSX). Cell lines expressing functional modified F(ab') antibody were identified by screening culture supernatants in an antigen binding ELISA format assay as described in our copending application. Cell lines expressing between 0.05–1 µg/ml modified F(ab') were obtained and subjected to screening for gene amplification by plating out in MSX concentrations ranging from 30–5000µM. Amplified cell lines growing in medium containing MSX at 200µM were found to express modified F(ab') to a level of 10–20µg/ml. One amplified cell line, 31.2 was used for further studies.

Purification of modified chimaeric F(ab')$_2$ Antibody

Hinge modified chimaeric F(ab') was purified from CHO cell supernatants using standard procedures. CHO cell culture supernatant containing modified chimaeric F(ab') was adjusted to 60% ammonium sulphate, the precipitate was resuspended in suitable buffer and passed over a DEAE-Sepharose column. Fractions containing F(ab')material were pooled and, after dialysis, passed over S-Sepharose. Fractions containing F(ab') material were pooled and then dialysed extensively into PBS and concentrated by ultrafiltration. By this process, the yield of F(ab')$_2$ is increased to approximately 40% of the finally purified material.

Hinge modified F(ab') was purified from CHO cell supernatant using immunopurification. An immunopurification reagent was prepared by linking NH3/41, an antibody with specificity for human Kappa chain sequence, to cyanogen bromide activated Sepharose by standard methodology. This material was packed into a column and requilibrated with PBS. CHO cell culture supernatant containing modified chimaeric F(ab') was applied to the column and the column was washed with PBS. Elution of modified chimaeric F(ab') was then achieved using 4.5 M guanidine hydrochloride. Fractions containing modified chimaeric F(ab') were then dialyzed extensively into PBS and concentrated by ultrafiltration. In repeat purifications, approximately 10% of the material can be found as F(ab')$_2$ which forms without further treatment.

Crosslinking of Modified Chimaeric F(ab')$_2$ Antibody

F(ab')$_2$ material from mouse B72.3, prepared by enzymatic digestion of whole antibody, and modified chimaeric F(ab') material prepared as described in the preceeding paragraph were chemically crosslinked by linking half-cysteine residues via thioether bonds with the use of the homo-bifunctionalcross-linking reagent 1,6 bismaleimidohexane (Sigma). B72.3 F(ab')$_2$ or modified chimaeric F(ab') at 1–5 mg/ml in 0.15M phosphate buffer pH8.0, containing 2 mM EDTA, was reduced by the addition of 2-mercaptoethylamine to a final concentration of 5 mM and incubated at 37° C. for 30 minutes. After reduction, samples were desalted on a Sephadex G25 column equilibrated with 0.1M citric acid/0.2M Na$_2$PO$_4$ pH6.0/2 mM EDTA. The crosslinker was dissolved in dimethylformamide in a final concentration of 72 mM and added to the freshly reduced F(ab')SH at a level of 1.9 mM (approx. 22 fold excess over titratable thiols) and incubated for 90 minutes with constant mixing. N-ethyl maleimide was added to a final concentration of 9 mM and incubated further for 30 minutes before desalting into 0.1M citric acid/0.2M Na$_2$PO$_4$ pH6.0/2 mM EDTA. The maleimidated F(ab'), (Fab')(MAL), was immediately added to a fresh batch of F(ab')SH at a molar ratio of 1.1:1.0 and incubated at room temperature with constant mixing for 20 hours.

The composition of the crosslinking reaction was determined by HPLC gel filtration after overnight incubation. 10µl of the reaction mixture was added to 10µl of 200 mM 2-mercaptoethylamine and incubated for 15 minutes. A further addition of 20µl of 800 mM iodoacetamide was made and incubated for 15 minutes. The reduced and alkylated sample was then analysed by HPLC GF 250 and the percentage composition of the chromatogram was determined by integration. Material eluting in the position of F(ab')$_2$ was assumed to be chemically crosslinked F(ab')$_2$. The elution times closely matched the expected F(ab')$_2$ retention times of various standards. The percentage crosslinking was higher for the chimaeric F(ab') material (one cysteine in the hinge) than for the mouse F(ab') material (three cysteines in the hinge) and contained less aggregated material. Reduction in the complexity of the hinge in this way may therefore lead to more efficient linking and superior product.

EXAMPLE 2

Chimaeric B72.3 IgG4 F(ab') (IgG1 Hinge)

Construction of F(ab') Heavy Chain Gene

To construct a hinge modified gene, the chimaeric F(ab) region containing the B72.3 VH/IgG4 gene was isolated as a 0.7 kbp fragment from JA 108 (described in our copending patent application PA 149) by treating the DNA with SalI, removing the 5' phosphate from the SalI site with calf intestinal phosphatase (CIP), and recurring the DNA with EcoRI.

The IgG1 hinge was assembled by preparing appropriate oligonucleotides to encode the IgG1 hinge. 500 pm of top and bottom strand oligonucleotide were kinase labelled and annealed by heating to 70° C. and cooling to room temperature in the kinase buffer. The hinge fragments were ligated to the 0.7 kbp fragment from JA108 prepared as above, and the CIP'ed 5' ends were kinased.

Assembly of Gene in Expression Vector

The chimaeric B72.3 F(ab') heavy chain gene fragment, assembled as described above, was subsequently cloned into the EcoRI/CIP treated vector of JA96 to give TR001. Expression of TR001 in suitable cells with an expression vector fragment capable of producing a useful light chain, for example chimaeric or humanised B72.3, will produce material which will assemble to give F(ab') and which will on suitable post translational modification in vivo or in vitro give F(ab')$_2$.

EXAMPLE 3

Chimaeric, B72.3 IgG4 F(ab')$_2$ (IgG2 Hinge)

Construction of F(ab') Heavy Chain Gene

To construct a hinge modified gene, the chimaeric F(ab) region containing the B72.3 VH/IgG4 was isolated as described in Example 2. The IgG2 hinge was assembled by kinase labelling 500 pm of top and bottom strand oligonucleotide and annealing the oligonucleotides by heating to 70° C. and cooling to room temperature in the kinase buffer. The hinge fragments were ligated to the 0.7 kbp fragment from JA108 prepared as above, and the CIP'ed 5' ends were kinased.

Assembly of Gene in Expression Vector

The chimaeric B72.3 F(ab') heavy chain gene fragment, assembled as described above was subsequently cloned into the EcoRI/CIP treated vector fragment of JA96 to give TR003. Expression of TR003 in suitable cells with an expression vector capable of producing a useful light chain, for example chimaeric or humanised B72.3, will produce material which will assemble to give F(ab') and which will on suitable post translational modification in vivo or in vitro give F(ab')$_2$.

EXAMPLE 4

Modifier B72.3 Chimaeric IgG4 F(ab')$_2$ (IgG3 Hinge) Construction of Modified F(ab') Heavy Chain Gene The IgG3 hinge is normally found as a reduplicated 4 exon structure which codes for a repeating sequence of the form ELKTPLGDTTHTCPRC[PEPKSCDTPPPCPRC]$_n$P where n normally is 3. Hinges of this form can be derived by correct ligation of the following oligonucleotides to the CH1 domain.

| | |
|---|---|
| 1. | 5' TCGACAAGAGAGTTGAGCTCAAAACCCCAC |
| 2. | 3' GTTCTCTCAATCGAGTTTTGGGGTGAACC |
| 3. | 5' TTGGTGACACACAACTCACACATGCCCACGGTG |
| 4. | 3' ACTGTGTTGAGTGTGTACGGGTGCCACGGGT |
| 5. | 5' CCCAGAGCCCAAATCTTGTGACACACCTCCCCCGTGCCCACGGTG |
| 6. | 3' CTCGGGTTTAGAACACTGTGTGGAGGGGGCACGGGTGCCACGGGGT |
| 7. | 5' CCCATGATG |
| 8. | 3' ACTACTTAA |

By suitable manipulation of the molar ratios of the oligonucleotides, n can be varied from 0 upwards to produce hinges of variable but predictable length and sequence.

To construct the IgG3 hinge, oligonucleotides were assembled by kinase labelling and annealing as in the previous Examples and ligating the relevant oligonucleotides to produce the correctly designed product. Because of the possibility of producing concatamers of the central oligonucleotide pair, the ligation products were cloned into pSP64 at the EcoRI and SalI sites. Miniprep DNA was prepared and cut with EcoRI, 3' labelled by filing the EcoRI end with $^{32}$P dATP using the Klenow polymerase, recutting the DNA with SalI and examining the length of the cloned inserts of polyacrylamide gels. A clone containing an insert of the required size to code for the IgG3 hinge was identified, the clone was grown up and the hinge insert isolated on a preparative scale. The hinge fragment was ligated to the 0.7 kbp fragment from JA108 prepared as above and the CIP'ed 5' ends were kinased to enable subsequent recloning.

Assembly of Gene in Expression Vector

The chimaeric B72.3 F(ab') heavy chain gene fragment, assembled as described above, was subsequently cloned into the EcoRI/CIP treated vector fragment of JA96 to give TR007. Expression of TR007 in suitable cells with an expression vector capable of producing a useful light chain, for example chimaeric or humanised B72.3, will produce material which will assemble to give F(ab') and which will on suitable post translational modification in vivo or in vitro give F(ab')$_2$.

EXAMPLE 5

Modified B72.3 Chimaeric IgG4 F(ab')$_2$ (IgG3 2 cys Hinge) Construction of F (ab') Heavy Chain Gene The IgG3 (2 cys) hinge length variant was assembled by kinase labelling and annealing as above and ligating the relevant oligonucleotides to produce the correct length product. The ligated products were cloned into pSP64 at the EcoRI and SalI sites. Miniprep DNA was prepared and cut with EcoRI, 3' labelled by filing the EcoRI end with $_{32}$P dATP using the Klenow polymerase, recurring the DNA with SalI and examining the length of the cloned inserts on polyacrylamide gels. A clone containing an insert of the required size to code for the IgG3(2 cys) hinge was identified, the clone was grown up and the hinge insert isolated on a preparative scale. The hinge fragments were ligated to the 0.7 kbp fragment from JA108 and the CIP'ed 5' ends were kinased to enable subsequent recloning.

Assembly of Gene in Expression Vector

The chimaeric B72.3 F(ab') heavy chain gene fragment, assembled as described above, was subsequently cloned into the EcoRI/CIP treated vector fragment of JA96 to give TR0004. Expression of TR0004 in suitable cells with an expression vector capable of producing a useful light chain, for example chimaeric or humanised B72.3, will produce material which will assemble to give F(ab') and which will on suitable post translational modification in vivo or in vitro give F(ab')$_2$.

EXAMPLE 6

Modified B72.3 Chimaeric IgG4 F(ab')$_2$ (IgG3 5 cys Hinge) Construction of F(ab') Heavy Chain Gene The IgG3 (5 cys) hinge length variant was assembled by kinase labelling annealing and ligating the relevant oligonucleotides as above to produce the correct length product. Because of the possibility of producing concatamers of the central oligonucleotide pair, the ligation products were cloned into pSP64 at the EcoRI and SalI sites. Miniprep DNA was prepared and cut with EcoRI 3' labelled by filing the EcoRI end with $_{32}$P dATP using the Klenow polymerase, recurring the DNA with SalI and examining the length of the cloned inserts on polyacrylamide gels. A clone containing an insert of the required size to code for the IgG3 (5 cys) hinge length variant was identified, the clone was grown up and the hinge insert isolated on a preparative scale. The ligated products were cloned into pSP64 at the EcoRI and SalI sites. The hinge fragments were ligated to the 0.7 kbp fragment from JA108 prepared as above and the CIP'ed ends were kinased to enable subsequent recloning.

Assembly of Gene in Expression Vector

The chimaeric B72.3 F(ab') heavy chain gene fragment, assembled as described above, was subsequently cloned into the EcoRI/CIP treated vector fragment of JA96 to give TR005 in suitable cells with an expression vector capable of producing a useful light chain, for example chimaeric or humanised B72.3, will produce material which will assemble to give F(ab') and which will on suitable post translational modification in vivo or in vitro give F(ab')$_2$.

EXAMPLE 7

Modified B72.3 Chimaeric IgG4 F(ab')$_2$ (IgG3 9 cys Hinge)
Construction of F(ab') Heavy Chain Gene The IgG3 (8 cys) hinge length variant was assembled by kinase labelling annealing and ligating the relevant oligonucleotides as above to produce the correct length product. Because of the possibility of producing concatamers of the central oligonucleotide pair, the ligation products were cloned into pSP64 at the EcoRI and SalI sites. Miniprep DNA was prepared and cut with EcoRI 3' labelled by filing the EcoRI end with $_3$ $_2$p dATP using the Klenow polymerase, recurring the DNA with SalI and examining the length of the cloned inserts on polyacrylamide gels. A clone containing an insert of the required size to code for the IgG3 (8 cys) hinge length variant was identified, the clone was grown up and the hinge insert isolated on a preparative scale. The ligated products were cloned into pSP64 at the EcoRI and SalI sites. The hinge fragments were ligated to the 0.7 kbp fragment from JA108 prepared as above and the CIP'ed ends were kinased to enable subsequent recloning.

Assembly of Gene in Expression Vector

The chimaeric B72.3 F(ab') heavy chain gene fragment, assembled as described above, was subsequently cloned into the EcoRI/CIP treated vector fragment of JA96 to give TR006 in suitable cells with an expression vector capable of producing a useful light chain, for example chimaeric or humanised B72.3, will produce material which will assemble to give F(ab') and which will on suitable post translational modification in vivo or in vitro give F(ab')$_2$.

It will be appreciated that the present invention has been described above by way of illustration only, and that variations or modifications of detail can be made without departing from the scope of the invention.

1. Kohler & Miisrein, Nature, 265, 495–497, 1975.
2. Ehrlich, P., Collected Studies on Immunity, 2, John Wiley & Sons, New York, 1906.
3. Levy a Miller, Ann. Rev.Med., 34, 107–116, 1983.
4. Schlom & Weeks, Important Advances in Oncology, 170–192, Wippincott, Philadelphia, 1985.
5. Colcher et al., PNAS, 78, 3199–3203, 1981.
6. Johnson et al., Cancer Res., 46, 850–897, 1986.
7. Stramignoni et al., Int. J.Cancer, 31, 543,552, 1983.
8. Nuti et al., Int.J.Cancer, 29, 539–545, 1982.
9. Thor et al., J.Nat. Cancer Inst., 76,995–1006, 1986.
10. Thor et al., Cancer Res., 46, 3118–3124, 1986.
11. Maniatis et al., Molecular Cloning, Cold Spring Harbor, N.Y., 1982.
12. Primrose and Old, Principles of Gene Manipulation, Blackwell, Oxford, 1980.

We claim:

1. An antibody molecule comprising heavy and light chains, each heavy chain having a hinge region, said hinge region having only one cysteine residue capable of forming a heavy chain to heavy chain disulphide bond, provided that the heavy chain is of a subclass which does not naturally contain a single cysteine residue capable of forming a heavy chain to heavy chain disulphide bond.

2. An antibody molecule comprising heavy and light chains, each heavy chain having a hinge region, said hinge region having from 2 to about 11 cysteine residues capable of forming heavy chain to heavy chain disulphide bonds, the number of hinge region cysteine residues being different than occurs naturally for heavy chains of the same subclass.

3. An Fab' fragment comprising a heavy chain and a light chain, said heavy chain having a hinge region, said hinge region having only one cysteine residue capable of forming a heavy chain to heavy chain disulphide bond, provided that the heavy chain is of a subclass which does not naturally contain a single cysteine residue capable of forming a heavy chain to heavy chain disulphide bond.

4. An Fab' fragment comprising a heavy chain and a light chain, said heavy chain having a hinge region, said hinge region having from 2 to about 11 cysteine residues capable of forming heavy chain to heavy chain disulphide bonds, the number of hinge region cysteine residues being different than occurs naturally for heavy chains of the same subclass.

5. An F(ab')$_2$ fragment comprising two Fab' fragments according to claim 3 linked together directly via said one hinge region cysteine residues.

6. An F(ab')$_2$ fragment comprising two Fab' fragments according to claim 4 linked together directly via said hinge region cysteine residues.

7. The antibody molecule of claim 1, further comprising an effector or reporter molecule attached to said hinge region.

8. The antibody molecule of claim 2, further comprising an effector or reporter molecule attached to said hinge region.

9. The Fab' fragment of claims 3, further comprising an effector or reporter molecule attached to said hinge region.

10. The Fab' fragment of claim 4, further comprising an effector or reporter molecule attached to said hinge region.

11. The F(ab')$_2$ fragment of claim 5, further comprising an effector or reporter molecule attached to said hinge region.

12. The F(ab')$_2$ fragment of claim 6, further comprising an effector or reporter molecule attached to said hinge region.

13. A humanised antibody molecule comprising heavy and light chains, each heavy chain having a hinge region, said hinge region having only one cysteine residue capable of forming a heavy chain to heavy chain disulphide bond "provided that the heavy chain is of a subclass which does not naturally contain a single cysteine residue capable of forming a heavy chain to heavy chain disulphide bond".

* * * * *

UNITED STATES PATENT AND TRADEMARK OFFICE
CERTIFICATE OF CORRECTION

PATENT NO. : 5,677,425
DATED : October 14, 1997
INVENTOR(S) : Bodmer et al.

It is certified that error appears in the above-identified patent and that said Letters Patent is hereby corrected as shown below:

Column 1,
Line 51, please delete "banding" and insert therefor -- binding --;

Column 2,
Line 41, please delete "rumour" and insert therefor -- tumour --;
Line 44, after "353,632" insert -- (PA 149) --;

Column 4,
Line 37, please delete "sequence" and insert therefor sequences --;
Line 57, please delete "sequence" and insert therefor sequences --;
Line 66, please delete "used" and insert therefor -- uses --;

Column 5,
Line 3, please delete "pre" and insert therefor -- per --;
Line 4, please delete "reference" and insert therefor -- references --;

Column 8,
Line 4, please delete "IaG4" and insert therefor -- IgG4 --;
Line 44, please delete "pgA115" and insert therefor -- pJA115 --;

Column 9,
Line 17, please delete "µg/mi" and insert therefor -- µg/ml --;
Line 40, please delete "requilibrated" and insert therefor -- equilibrated --;
Line 56, please delete "bifunctionalcross" and insert therefor -- bifunctional cross --;
Line 10, please delete "of200" and insert therefor -- of 200 --;
Line 28, please delete "F(ab')" and insert therefor -- F(ab')$_2$ --;

Column 11,
Line 15, please delete "Modifier" and insert therefor -- Modified --;

Column 12,
Line 10, please delete "$_{32}$P" and insert therefor -- $^{32}$P --;
Line 54, please delete "$_{32}$P" and insert therefor -- $^{32}$P --;

UNITED STATES PATENT AND TRADEMARK OFFICE
CERTIFICATE OF CORRECTION

PATENT NO. : 5,677,425
DATED : October 14, 1997
INVENTOR(S) : Bodmer et al.

It is certified that error appears in the above-identified patent and that said Letters Patent is hereby corrected as shown below:

Column 13,
Line 10, please delete "(IgG3 9 cys Hinge)" and insert therefor -- (IgG3 8 cys Hinge) --;
Line 20, please delete "$_{32}P$" and insert therefor -- $^{32}P$ --;
Line 46, please delete "Miisrein" and insert therefor -- Milstein --;
Line 49, please "Levy a Miller" and insert therfor -- Levy & Miller --.

Signed and Sealed this

Eighteenth Day of December, 2001

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.   : 5,677,425
DATED        : October 14, 1997
INVENTOR(S)  : Bodmer et al.

It is certified that error appears in the above-identified patent and that said Letters Patent is hereby corrected as shown below:

Column 1,
Line 51, please delete "banding" and insert therefor -- binding --;

Column 2,
Line 41, please delete "rumour" and insert therefor -- tumour --;
Line 44, after "353,632" insert -- (PA 149) --;

Column 4,
Line 37, please delete "sequence" and insert therefor sequences --;
Line 57, please delete "sequence" and insert therefor sequences --;
Line 66, please delete "used" and insert therefor -- uses --;

Column 5,
Line 3, please delete "pre" and insert therefor -- per --;
Line 4, please delete "reference" and insert therefor -- references --;

Column 8,
Line 4, please delete "IaG4" and insert therefor -- IgG4 --;
Line 44, please delete "pgA115" and insert therefor -- pJA115 --;

Column 9,
Line 17, please delete "$\mu$g/mi" and insert therefor -- $\mu$g/ml --;
Line 40, please delete "requilibrated" and insert therefor -- equilibrated --;
Line 56, please delete "bifunctionalcross" and insert therefor -- bifunctional cross --;

Column 10,
Line 10, please delete "of200" and insert therefor -- of 200 --;
Line 28, please delete "F(ab')" and insert therefor -- $F(ab')_2$ --;

Column 11,
Line 15, please delete "Modifier" and insert therefor -- Modified --;

Column 12,
Line 10, please delete "$_{32}$P" and insert therefor -- $^{32}$P --;
Line 54, please delete "$_{32}$P" and insert therefor -- $^{32}$P --;

UNITED STATES PATENT AND TRADEMARK OFFICE
CERTIFICATE OF CORRECTION

PATENT NO.    : 5,677,425
DATED         : October 14, 1997
INVENTOR(S)   : Bodmer et al.

It is certified that error appears in the above-identified patent and that said Letters Patent is hereby corrected as shown below:

Column 13,
Line 10, please delete "(IgG3 9 cys Hinge)" and insert therefor -- (IgG3 8 cys Hinge) --;
Line 20, please delete "$_{32}P$" and insert therefor -- $^{32}P$ --;
Line 46, please delete "Miisrein" and insert therefor -- Milstein --;
Line 49, please "Levy a Miller" and insert therfor -- Levy & Miller --.

This certificate supersedes Certificate of Correction issued December 18, 2001

Signed and Sealed this

Second Day of December, 2003

JAMES E. ROGAN
*Director of the United States Patent and Trademark Office*

UNITED STATES PATENT AND TRADEMARK OFFICE
CERTIFICATE OF CORRECTION

PATENT NO.     : 5,677,425
DATED          : October 14, 1997
INVENTOR(S)    : Bodmer et al.

It is certified that error appears in the above-identified patent and that said Letters Patent is hereby corrected as shown below:

Column 1,
Line 51, please delete "banding" and insert therefor -- binding --;

Column 2,
Line 41, please delete "rumour" and insert therefor -- tumour --;
Line 44, after "353,632" insert -- (PA 149) --;

Column 4,
Line 37, please delete "sequence" and insert therefor sequences --;
Line 57, please delete "sequence" and insert therefor sequences --;
Line 66, please delete "used" and insert therefor -- uses --;

Column 5,
Line 3, please delete "pre" and insert therefor -- per --;
Line 4, please delete "reference" and insert therefor -- references --;

Column 8,
Line 4, please delete "IaG4" and insert therefor -- IgG4 --;
Line 44, please delete "pgA115" and insert therefor -- pJA115 --;

Column 9,
Line 17, please delete "$\mu$g/mi" and insert therefor -- $\mu$g/ml --;
Line 40, please delete "requilibrated" and insert therefor -- equilibrated --;
Line 56, please delete "bifunctionalcross" and insert therefor -- bifunctional cross --;

Column 10,
Line 10, please delete "of200" and insert therefor -- of 200 --;
Line 28, please delete "F(ab')" and insert therefor -- $F(ab')_2$ --;

Column 11,
Line 15, please delete "Modifier" and insert therefor -- Modified --;

Column 12,
Line 10, please delete "$_{32}$P" and insert therefor -- $^{32}P$ --;
Line 54, please delete "$_{32}$P" and insert therefor -- $^{32}P$ --;

UNITED STATES PATENT AND TRADEMARK OFFICE
CERTIFICATE OF CORRECTION

PATENT NO. : 5,677,425
DATED : October 14, 1997
INVENTOR(S) : Bodmer et al.

It is certified that error appears in the above-identified patent and that said Letters Patent is hereby corrected as shown below:

<u>Column 13,</u>
Line 10, please delete "(IgG3 9 cys Hinge)" and insert therefor -- (IgG3 8 cys Hinge) --;
Line 20, please delete "$_{32}P$" and insert therefor -- $^{32}P$ --;
Line 46, please delete "Miisrein" and insert therefor -- Milstein --;
Line 49, please "Levy a Miller" and insert therfor -- Levy & Miller --.

This certificate supersedes Certificate of Correction issued December 2, 2003.

Signed and Sealed this

Twenty-fifth Day of May, 2004

JON W. DUDAS
*Acting Director of the United States Patent and Trademark Office*